United States Patent
Lopes Da Silva et al.

(10) Patent No.: US 10,821,120 B2
(45) Date of Patent: Nov. 3, 2020

(54) METHOD FOR CONTROLLING NEUROINFLAMMATION

(71) Applicant: N.V. NUTRICIA, Zoetermeer (NL)

(72) Inventors: Sofia Lopes Da Silva, Groningen (NL); Ladislaus Maria Broersen, Utrecht (NL); Robert Johan Joseph Hageman, Utrecht (NL); Jan Maarten Verkuijl, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 16/308,370

(22) PCT Filed: Jun. 9, 2017

(86) PCT No.: PCT/NL2017/050380
§ 371 (c)(1),
(2) Date: Dec. 7, 2018

(87) PCT Pub. No.: WO2017/213504
PCT Pub. Date: Dec. 14, 2017

(65) Prior Publication Data
US 2019/0175622 A1    Jun. 13, 2019

(30) Foreign Application Priority Data

Jun. 10, 2016  (WO) ................ PCT/NL2016/050419

(51) Int. Cl.
| | | |
|---|---|---|
| *A61K 31/593* | (2006.01) | |
| *A61K 31/07* | (2006.01) | |
| *A61K 31/202* | (2006.01) | |
| *A61K 31/4415* | (2006.01) | |
| *A61K 31/714* | (2006.01) | |
| *A61K 31/519* | (2006.01) | |
| *A61P 29/00* | (2006.01) | |
| *A61K 31/14* | (2006.01) | |
| *A61K 31/355* | (2006.01) | |
| *A61K 31/375* | (2006.01) | |

(52) U.S. Cl.
CPC ............ *A61K 31/593* (2013.01); *A61K 31/07* (2013.01); *A61K 31/202* (2013.01); *A61K 31/4415* (2013.01); *A61K 31/519* (2013.01); *A61K 31/714* (2013.01); *A61P 29/00* (2018.01); *A61K 31/14* (2013.01); *A61K 31/355* (2013.01); *A61K 31/375* (2013.01)

(58) Field of Classification Search
None
See application file for complete search history.

(56) References Cited

FOREIGN PATENT DOCUMENTS

| WO | WO 2007/104030 A1 | 9/2007 | |
|---|---|---|---|
| WO | WO 2016/016790 A1 | 2/2016 | |
| WO | WO 2016/072842 A1 | 5/2016 | |
| WO | WO-2016072842 A1 * | 5/2016 | ............. A61K 31/14 |

OTHER PUBLICATIONS

Lalancette-Hebert et al., Accumulation of dietary docosahexaenoic acid in the brain attenuates acute immune response and development of postischemic neuronal damage, Stroke, Oct. 2011;42(10):2903-9.*
Reagan-Shaw et al., Dose translation from animal to human studies revisited, The FASEB Journal, vol. 22, Mar. 2007, 659-661.*
Adzemovic et al., Efficacy of vitamin D in treating multiple sclerosis-like neuroinflammation depends on developmental stage, Exp Neurol. Nov. 2013;249:39-48.*
Piguet, Neurodegenerative disease: Frontotemporal dementia—time to target inflammation?, Nature Reviews. Neurology; London vol. 9, Iss. 6, (Jun. 2013): 304-305.*
Lalancette-Hebert et al., "Accumulation of Dietary Docosahexaenoic Acid in the Brain Attenuates Acute Immune Response and Development of Postischemic Neuronal Damage", Stroke I AHA/ASA Journals, vol. 42, Oct. 1, 2011, pp. 2903-2909.
Adzemovic et al., "Efficacy of vitamin D in treating multiple sclerosis-like neuroinflammation depends on developmental stage", Experimental Neurology, vol. 249, Nov. 1, 2013, pp. 39-48.
Kurtysi et al., "The combination of vitamins and omega-3 fatty acids has an enhanced anti-inflammatory effect on microglia", Neurochemistry International, vol. 99, Jul. 25, 2016, pp. 206-214.
International Search Report issued in PCT/NL2017/050380, dated Sep. 15, 2017.
Written Opinion of the International Searching Authority issued in PCT/NL2017/050380, dated Sep. 15, 2017.

* cited by examiner

*Primary Examiner* — Svetlana M Ivanova
(74) *Attorney, Agent, or Firm* — N.V. Nederlandsch Octrooibureau; Catherine A. Shultz; Katelyn J. Bernier

(57) ABSTRACT

The invention pertains to the use of therapeutically effective amounts of (i) vitamin A and/or functional equivalents, (ii) vitamin D and/or functional equivalents, and (iii) at least one omega-3 PUFA, preferably DHA and/or EPA, more preferably DHA and EPA, for the manufacture of a composition or medicament for treating, reducing and/or preventing neuroinflammation and/or symptoms associated with neuroinflammation in a subject in need thereof, as well as for reducing microglia activation, and/or for treating, reducing and/or preventing symptoms associated with excessive activation of microglia; and/or for reducing the secretion of inflammatory cytokines, preferably IL-6, and/or for treating, reducing and/or preventing symptoms associated with excessive secretion of inflammatory cytokines, in a subject in need thereof.

14 Claims, 2 Drawing Sheets

METHOD FOR CONTROLLING NEUROINFLAMMATION

CROSS-REFERENCE TO RELATED APPLICATIONS

Figure 1A:
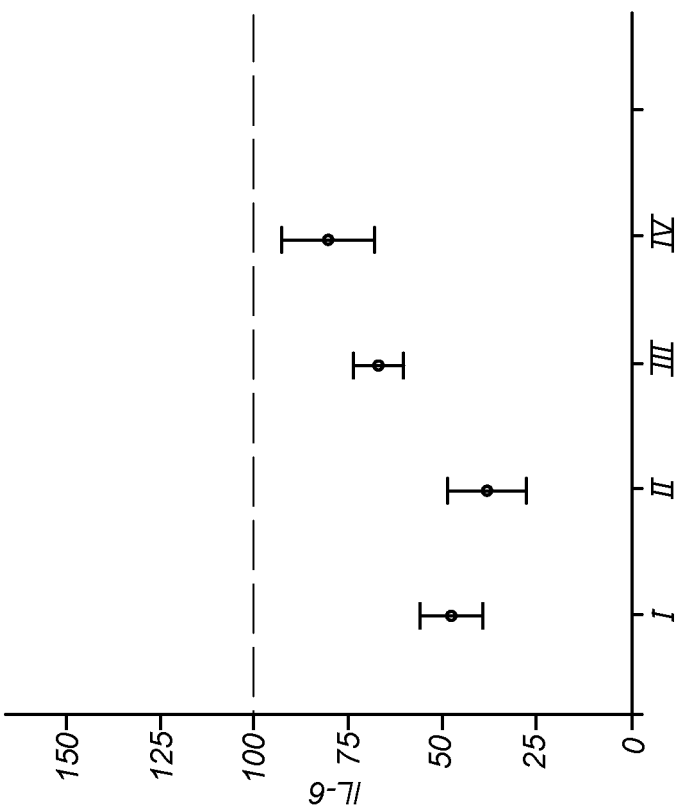

This application is the National Phase of International Patent Application No. PCT/NL2017/050380, filed Jun. 9, 2017, published on Dec. 14, 2017 as WO 2017/213504 A1, which claims priority to International Patent Application No. PCT/NL2016/050419, filed Jun. 10, 2016. The contents of these applications are herein incorporated by reference in their entirety.

The invention is in the field of medical nutrition and more particularly relates to compositions for use in treating or controlling and/or preventing and/or reducing the risk of (chronic or excessive) inflammation of the central nervous system (CNS).

BACKGROUND TO THE INVENTION

Neuroinflammation is a response of the innate immune system of the CNS that is associated with many disorders, including depression, schizophrenia, Alzheimer's disease (AD), Parkinson's disease and Multiple Sclerosis (MS), postoperative cognitive dysfunction (POCD), spinal cord injury (SCI), AIDS dementia complex (ADC), ischemia, stroke, traumatic brain injury (TBI), infection of the brain or central nervous system, brain tumours. Microglia cells are thought to be the main important cell type involved in neuroinflammation. Microglia are the innate immune cells of the central nervous system, which act quickly on neuroinflammation. However, prolonged activation of microglia, as in chronic or acute neuroinflammation, causes damage to brain tissue and to the blood-brain-barrier, causing neurodegenerative disorders.

The possible effect of diet on the incidence of brain diseases in which neuroinflammation plays a role is put forward by Lourida et al. (*Epidemiology*, 2013, 24, 479-489), Skarupski et al. (*J. Nutr. Health Aging*, 2013, 17, 441-445) and Jacka et al. (*Am. J. Psychiatry*, 2010, 167, 305-311. Possible protective effects of specific nutrients have also been investigated, e.g. for n-3 LC-PUFAs (US 2003/0050341; Labrousse et al., *PLoS* One, 2012, 7, e36861; Laye et al., OCL, 2011, 18, 301-306; Lalancette-Hebert, *Stroke*, 2011, 42, 2903-2909) or for vitamin D (US 2012/0128711; Adzemovic et al., *Exp. Neurol.* 2013, 249, 39-48; Amor, *CNS and Neurological Disorders*, 2010, 9, 524).

Vitamin A, on the other hand, has been suggested to increase the content of receptor for advanced glycation end products (RAGE) in rats cerebral cortices (Roberto de Oliviera, *An. Acad. Bras. Ciênc.* 2015, 87(2 Suppl.), 1361-1373).

In the art there is a continuous need for improving treatment and control of neuroinflammation.

SUMMARY OF THE INVENTION

The inventors surprisingly found that a combination of (i) vitamin A, (ii) vitamin D and (iii) polyunsaturated fatty acids (PUFAs) is effective in treating (controlling), reducing and/or preventing detriment neuroinflammation, and/or treating (controlling), reducing and/or preventing symptoms associated with detriment neuroinflammation. Compared to the individual ingredients, the combination reduces microglia activation and treats, reduced or prevents symptoms associated with excessive activation of microglia, and reduces the secretion of inflammatory cytokines. Surprising reductions have been observed using the combination even at dosages at which the individual components do not show any effect. One of the benefits is thus that dosages (e.g. daily dose) of the individual components can be reduced without compromising the therapeutical effectivity of the combination according to the invention.

In the context of the invention, the effects achieved by the inventors are considered advantageous to therapeutically treat or prevent neuroinflammation which is considered detriment to the subject's health, thus generally referred to as 'detriment neuroinflammation'. Neuroinflammation is thus therapeutically controlled such that it does not cause harm to the subject's health.

These findings are particularly relevant to stroke-induced or stroke-associated neuroinflammation. In a preferred embodiment, vitamins A and D, including their equivalents, and at least one omega-3 PUFA, preferably DHA and/or EPA, more preferably at least DHA, even more preferably DHA and EPA, are made part of a composition. These components (i), (ii) and (iii) are present in therapeutically effective amounts.

More in particular, the combination or composition according to the invention has been found surprisingly effective in reducing NO and IL-6 release from activated microglia, which is a direct indication of reduced neuroinflammation. The therapeutic combination of (i) vitamin A, (ii) vitamin D and (iii) DHA and EPA was found to act synergistically, providing a marked reduction in NO and IL-6 release where the individual components in the same concentration did not show such a reduction. A clear reducing trend was observed when assessing IL-6 release, and a significant reduction in NO release was found. Without wishing to being bound to any theory, the inventors believe that each of the individual nutrients (i) vitamin A, (ii) vitamin D and (iii) omega-3 PUFA, preferably DHA and EPA, act on convergent pathways involved in neuroinflammation, and the combination yields a synergistic effect.

Associated therewith, the present invention thus concerns a (therapeutic) method for treating, reducing and/or preventing neuroinflammation, or symptoms associated with neuroinflammation, in a subject in need thereof, comprising administering to the subject a composition or combination comprising therapeutically effective amounts of (i) vitamin A, (ii) vitamin D and (iii) at least one omega-3 PUFA, preferably DHA and/or EPA, more preferably at least DHA, even more preferably DHA and EPA. Detriment neuroinflammation is thus (prophylactically) treated. The invention may also be worded as the use of therapeutically effective amounts of (i) vitamin A, (ii) vitamin D and (iii) at least one omega-3 PUFA, preferably DHA and/or EPA, more preferably at least DHA, even more preferably DHA and EPA, for the manufacture of a composition or medicament for treating, reducing and/or preventing neuroinflammation and/or symptoms associated with neuroinflammation in a subject in need thereof. In other words, the invention concerns a composition for therapeutic use in treating, reducing and/or preventing neuroinflammation, and/or symptoms associated with neuroinflammation in a subject in need thereof, said composition comprising therapeutically effective amounts of (i) vitamin A, (ii) vitamin D and (iii) at least one omega-3 PUFA, preferably DHA and/or EPA, more preferably at least DHA, even more preferably DHA and EPA. The invention also concerns a combination of (i) vitamin A and/or functional equivalents, (ii) vitamin D and/or functional equivalents, and (iii) at least one omega-3 PUFA, preferably DHA and/or EPA, more preferably DHA and EPA, (i), (ii) and (iii) being in therapeutically effective amounts, for therapeutic use in treating, reducing and/or preventing neuroinflammation, and/or symptoms associated with neuroinflammation in a subject in need thereof. The combination is preferably comprised in a composition and/or administered in the form of a composition. The (prophylactic) treatment preferably involves reducing microglia activation and/or reducing the secretion of inflammatory cytokines, preferably IL-6.

Associated therewith, the invention also pertains to a (therapeutic) method for reducing microglia activation, and/or for treating, reducing and/or preventing symptoms associated with excessive activation of microglia; and/or for reducing the secretion of inflammatory cytokines, preferably IL-6, and/or for treating, reducing and/or preventing symptoms associated with excessive secretion of inflammatory cytokines, in a subject in need thereof, comprising administering to the subject a composition or combination comprising therapeutically effective amounts of (i) vitamin A, (ii) vitamin D and (iii) at least one omega-3 PUFA, preferably DHA and/or EPA, more preferably DHA and EPA. Worded differently, the invention also pertains to the use of therapeutically effective amounts of (i) vitamin A, (ii) vitamin D and (iii) at least one omega-3 PUFA, preferably DHA and/or EPA, more preferably at least DHA, even more preferably DHA and EPA, for the manufacture of a composition or medicament for reducing microglia activation, and/or for treating, reducing and/or preventing symptoms associated with excessive activation of microglia; and/or for reducing the secretion of inflammatory cytokines, preferably IL-6, and/or for treating, reducing and/or preventing symptoms associated with excessive secretion of inflammatory cytokines, in a subject in need thereof. Also, the invention concerns a composition for therapeutic use in for reducing microglia activation, and/or for treating, reducing and/or preventing symptoms associated with excessive activation of microglia; and/or for reducing the secretion of inflammatory cytokines, preferably IL-6, and/or for treating, reducing and/or preventing symptoms associated with excessive secretion of inflammatory cytokines, in a subject in need thereof, said composition comprising therapeutically effective amounts of (i) vitamin A, (ii) vitamin D and (iii) at least one omega-3 PUFA, preferably DHA and/or EPA, more preferably at least DHA, even more preferably DHA and EPA. The components (i), (ii) and (iii) are present in therapeutically effective amounts. Also, the invention concerns a combination of (i) vitamin A and/or functional equivalents, (ii) vitamin D and/or functional equivalents, and (iii) at least one omega-3 PUFA, preferably DHA and/or EPA, more preferably DHA and EPA, (i), (ii) and (iii) being in therapeutically effective amounts, for therapeutic use in for reducing microglia activation, and/or for treating, reducing and/or preventing symptoms associated with excessive activation of microglia; and/or for reducing the secretion of inflammatory cytokines, preferably IL-6, and/or for treating, reducing and/or preventing symptoms associated with excessive secretion of inflammatory cytokines, in a subject in need thereof. The combination is preferably comprised in a composition and/or administered in the form of a composition.

In a preferred embodiment, the present method, use, combination or composition for use involves treating, reducing and/or preventing neuroinflammation in a subject in need thereof, preferably treating neuroinflammation in a subject in need thereof, particularly neuroinflammation in a subject suffering from stroke or being at increased risk of stroke, including subjects at increased risk of recurring stroke.

Preferred Embodiments

1. Use of therapeutically effective amounts of (i) vitamin A and/or functional equivalents, (ii) vitamin D and/or functional equivalents, and (iii) at least one omega-3 PUFA, preferably DHA and/or EPA, more preferably DHA and EPA, for the manufacture of a composition or medicament for treating, reducing and/or preventing neuroinflammation and/or symptoms associated with neuroinflammation in a subject in need thereof
2. Use according to embodiment 1, said neuroinflammation being associated with a disorder selected from depression, schizophrenia, Alzheimer's disease (AD), Parkinson's disease, Multiple Sclerosis (MS), postoperative cognitive dysfunction (POCD), spinal cord injury (SCI), AIDS dementia complex (ADC), ischemia, stroke, traumatic brain injury (TBI), infection of the brain or central nervous system and brain tumours and/or said subject suffering from one or more disorders selected from depression, schizophrenia, Alzheimer's disease (AD), Parkinson's disease, Multiple Sclerosis (MS), postoperative cognitive dysfunction (POCD), spinal cord injury (SCI), AIDS dementia complex (ADC), ischemia, stroke, traumatic brain injury (TBI), infection of the brain or central nervous system and brain tumours.
3. Use according to embodiment 2, said disorder being selected from Alzheimer's disease (AD), postoperative cognitive dysfunction (POCD) and stroke.
4. Use according to embodiment 3, said neuroinflammation being stroke-associated neuroinflammation and/or said subject suffering from stroke or being at increased risk of stroke, preferably at increased risk of recurrent stroke.
5. Use according to any one of the preceding embodiments, said neuroinflammation being chronic neuroinflammation.
6. Use according to any one of the preceding embodiments, said treating, reducing and/or treating and/or preventing involving reduction of the intensity of neuroinflammation and/or reduction of the duration of neuroinflammation.
7. Use according to any one of the preceding embodiments, said treating, reducing and/or preventing involving reduction of microglia activation and/or reduction of the secretion of inflammatory cytokines, preferably of TNF-α and/or IL-6.
8. Use according to any one of the preceding embodiments, wherein vitamin A and/or functional equivalents is administered in a daily dose of 0.05-3 mg/day, preferably 0.5-1.5 mg/day.
9. Use according to any one of the preceding embodiments, wherein vitamin D and/or functional equivalents is administered in a daily dose of 0.1-100 μg/day, preferably 5-15 μg/day.
10. Use according to any one of the preceding embodiments, wherein omega-3 PUFA is administered in a daily dose of 500 to 5000 mg.
11. Use according to any one of the preceding embodiments, wherein DHA is administered in a daily dose of 0.05-5 g/day, preferably 0.5-1.5 g/day.
12. Use according to any one of the preceding embodiments, wherein the composition further comprises choline, and preferably further comprises B vitamin(s).

13. Use according to any one of the preceding embodiments, wherein the composition further comprises phospholipids, choline, B vitamin(s) and antioxidants.
14. A method for treating, reducing and/or preventing neuroinflammation, or symptoms associated with neuroinflammation, in a subject in need thereof, comprising administering to the subject a composition or combination comprising therapeutically effective amounts of (i) vitamin A and/or functional equivalents, (ii) vitamin D and/or functional equivalents, and (iii) at least one omega-3 PUFA, preferably DHA and/or EPA, more preferably DHA and EPA.
15. A composition for therapeutic use in treating, reducing and/or preventing neuroinflammation, and/or symptoms associated with neuroinflammation in a subject in need thereof, said composition comprising therapeutically effective amounts of (i) vitamin A and/or functional equivalents, (ii) vitamin D and/or functional equivalents, and (iii) at least one omega-3 PUFA, preferably DHA and/or EPA, more preferably DHA and EPA.
16. Combination of (i) vitamin A and/or functional equivalents, (ii) vitamin D and/or functional equivalents, and (iii) at least one omega-3 PUFA, preferably DHA and/or EPA, more preferably DHA and EPA, (i), (ii) and (iii) being in therapeutically effective amounts, for therapeutic use in treating, reducing and/or preventing neuroinflammation, and/or symptoms associated with neuroinflammation in a subject in need thereof.

The subject-matter of preferred embodiments 2-13 (e.g. medical indications, dosage, compounds/ingredients) also applies to the method according to embodiment 14, the composition of embodiment 15 and the combination of embodiment 16.

DETAILED DESCRIPTION

The inventors surprisingly found that the combination of vitamin A, vitamin D, EPA and DHA is effective in attenuating NO release from LPS-stimulated BV-2 cells. In activated immune cells, NO is produced from L-arginine by a reaction catalysed by iNOS. The expression of iNOS is mainly activated by the transcription factor NF-kappaB. Excessive NO production has been shown to cause a neurotoxic effect. NO mediates glutamate neurotoxicity and has been shown to be present in several brain pathologies, including neurodegenerative diseases. The ability to suppress excessive NO release by activated immune cells is widely used as an indicator of anti-inflammatory efficacy. The inventors also found that the combination of vitamin A, vitamin D, EPA and DHA is effective in attenuating IL-6 release from LPS-stimulated BV-2 cells. Increased levels of IL-6 have been correlated with disease severity, and new treatment strategies for inflammatory diseases focusing on blocking IL-6 signalling are being developed. Based on these unexpected findings, compared to the effects achieved with the individual components, the invention pertains to the use of vitamins A and D, and their equivalents, and omega-3 polyunsaturated fatty acids, preferably EPA and DHA, in combinations, compositions for use or methods for treating conditions associated with excessive NO and/or IL-6 production.

Composition

The method, use, combination or composition for use according to the invention involves administration of the composition according to the invention. The composition according to the invention may be used as a pharmaceutical product or a nutritional product, preferably the composition is a nutritional product or supplement.

In one aspect, the composition according to the invention may be used as a pharmaceutical product comprising one or more pharmaceutically acceptable carrier materials. Such product may contain the daily dosages as defined below in one or more dosage units. The dosage unit may be in a liquid form or in a solid form, wherein in the latter case the daily dosage may be provided by one or more solid dosage units, e.g. in one or more capsules or tablets. The pharmaceutical product, preferably for enteral application, may be a solid or liquid galenical formulation. Examples of solid galenical formulations are tablets, capsules (e.g. hard or soft shell gelatine capsules), pills, sachets, powders, granules and the like which contain the active ingredients together with conventional galenical carriers. Any conventional carrier material can be utilized. The carrier material can be organic or inorganic inert carrier material suitable for oral administration. Suitable carriers include water, gelatine, gum Arabic, lactose, starch, magnesium stearate, talc, vegetable oils, and the like. Additionally, additives such as flavouring agents, preservatives, stabilizers, emulsifying agents, buffers and the like may be added in accordance with accepted practices of pharmaceutical compounding. While the individual active ingredients are suitably administered in a single composition, they may also be administered in individual dosage units.

In a preferred aspect, the composition according to the invention may be (used as) a nutritional product, for example a nutritional supplement, which can be (used as) e.g. an additive to a normal diet, a fortifier, or a complete nutrition. The nutritional product preferably comprises at least one component, preferably all components, selected from the group consisting of fats, proteins, and carbohydrates. It is understood that a nutritional product differs from a pharmaceutical product by the presence of nutrients which provide nutrition to the subject to which the composition is administered, in particular the presence of protein, fat, digestible carbohydrate and/or dietary fibre.

In one embodiment, the product further comprises carbohydrates and/or proteins, wherein the lipid fraction provides between 10 and 95 energy % of the food product, preferably between 20 and 50 energy %, more preferably between 20 and 45 en %, even more preferably between 25-45 en %, most preferably 30-40 en %. In one embodiment, the food product is a liquid composition containing more than 0.5 kcal per ml, preferably more than 0.8 kcal per ml, preferably 1.0 kcal per ml or more, or 1.5 kcal per ml or more, or even 2 kcal per ml or more. In one embodiment, the food product is a liquid composition containing between 0.5 kcal per ml and 2.5 kcal, preferably between 0.5 kcal per ml and 2.5 kcal.

The composition of the invention is typically an enteral composition, i.e. intended for oral administration. It is preferably administered in liquid form. Preferably, the composition comprises water in which the components are dissolved and/or suspended.

The composition is preferably a liquid. Alternatively, the composition is a solid (typically a powder or a tablet, preferably a powder) which is possibly reconstitutable with a liquid, preferably with water, to obtain a liquid composition.

Dosages of components defined therein may for example be in daily dose or in a concentration per 100 ml. The latter definition also applies to reconstitution powders in which case these amounts are to be determined after reconstitution with the liquid.

Vitamin A

The present use, method, composition or combination involves (i) vitamin A, including functional equivalents thereof. Any functional form of vitamin A known in the art is suitable to be used, including retinol (in particular retinol esters), retinal, retinoic acid, beta-carotene, provitamin A, or any combination thereof. Preferably, the composition comprises retinol, in particular retinyl acetate and/or retinyl palmitate.

Vitamin A is advantageously administered in a daily dose of 0.05-3 mg/day, preferably 0.1-2.5 mg/day, more preferably 0.1-2 mg/day, even more preferably 0.5-1.5 mg/day, or 0.1-1 mg/day, even more preferably 0.2-0.8 mg/day, most preferably 0.2-0.5 mg/day. Doses are given based on retinol activity equivalents (RAE), for adults in particular, and the skilled person is capable to determine the dose for children. Moreover the skilled person is capable to determine the dose of a retinol equivalent. Retinol activity equivalent is typically defined as 1 microgram RAE being equivalent to 1 microgram retinol or 12 microgram beta-carotene. The amount of vitamin A in the composition or combination according to the invention is preferably such that the aforementioned daily doses are obtained. Such a content of vitamin A is especially suited in order to achieve the effects according to the invention, while ingesting relatively low amounts of the composition. Vitamin A is typically used in a therapeutically effective amount.

In one embodiment, the present invention concerns the use of vitamin A as defined herein, preferably in combination with vitamin D or a functional equivalent thereof, and/or at least one omega-3 PUFA, preferably DHA and/or EPA, for therapeutic use against neuroinflammation as defined herein, and preferably in amounts as detailed herein.

Vitamin D

The present use, method, composition or combination involves (ii) vitamin D, including functional equivalents thereof. Vitamin D is a group of fat-soluble secosteroids responsible for enhancing intestinal absorption of calcium, iron, magnesium, phosphate and zinc. In humans, the most important compounds in this group are vitamin $D_3$ (also known as cholecalciferol) and vitamin $D_2$ (ergocalciferol). Cholecalciferol and ergocalciferol—known collectively as "calciferol"—can be ingested from the diet and from supplements. The body can also synthesize vitamin D (specifically cholecalciferol) in the skin, from cholesterol, when sun exposure is adequate. Any functional form of vitamin D known in the art is suitable to be used, including vitamin D1, vitamin D2, vitamin D3, vitamin D4, vitamin D5, or any combination thereof. Preferably, the composition comprises vitamin D2 and/or vitamin D3, more preferably vitamin D3.

Vitamin D, also known as calciferol, comprises a group of fat-soluble secosteroids responsible for enhancing intestinal absorption of calcium, iron, magnesium, phosphate and zinc. In humans, the most important compounds in this group are vitamin D3 (also known as cholecalciferol) and vitamin D2 (ergocalciferol). Cholecalciferol and ergocalciferol can be ingested from the diet and from supplements. The body can also synthesize vitamin D (specifically cholecalciferol) in the skin, from cholesterol, when sun exposure is adequate. Any functional form of vitamin D known in the art is suitable to be used, including vitamin D1, vitamin D2, vitamin D3, vitamin D4, vitamin D5, or any combination thereof. Preferably, the composition comprises vitamin D2 and/or vitamin D3, more preferably vitamin D2. Vitamin D is advantageously administered in a daily dose of 0.1-100 µg/day, preferably 1-50 µg/day, more preferably 1-25 µg/day, more preferably 1-20 µg/day, more preferably 5-15 µg/day. The amount of vitamin D in the composition according to the invention is preferably such that the aforementioned daily doses are obtained. The amount of vitamin D in the use, method, composition according to the invention is preferably 1.3 to 40, more preferably 1.8 to 34, most preferably 2.0 to 28 microgram per 100 g of the composition. Such a content of vitamin D are especially suited in order to achieve the effects according to the invention, while ingesting relatively low amounts of the composition. Vitamin D is typically used in therapeutically effective amounts.

In one embodiment, the present invention concerns the use of vitamin D as defined herein, preferably in combination with vitamin A or a functional equivalent thereof, and/or at least one omega-3 PUFA, preferably DHA and/or EPA, for therapeutic use against neuroinflammation as defined herein, and preferably in amounts as detailed herein.

PUFA

The present composition or combination comprises (iii) at least one omega-3 long-chain polyunsaturated fatty acid (PUFA). In the context of the present invention, LC-PUFAs (long-chain PUFAs) have a chain length of 18 or more carbon atoms. Although one PUFA may be present, at is preferred that at least two different PUFAs are present. The PUFA is preferably selected from docosahexaenoic acid (22:6; DHA), eicosapentaenoic acid (20:5; EPA), docosapentaenoic acid (22:5 ω-3; DPA) and mixtures thereof, preferably at least one of DHA and EPA, even more preferably at least DHA. Preferably the present composition or combination contains at least therapeutically effective amounts of DHA, more preferably of DHA and of EPA. DHA was found to have a significant effect on reducing NO release, but this effect was further enhanced when DHA was combined with EPA. The PUFA is preferably used in combination with vitamins A and vitamin D, including their functional equivalents.

The PUFAs are preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present composition comprises at least DHA in triglyceride form. Suitable (n-3) PUFA sources include marine oil (e.g. fish oil, algae oil, or krill oil), DHA-rich alkyl esters, egg yolk, or phospholipids enriched with (n-3) LC-PUFA e.g. phosphatidylserine-DHA. Preferably, a (n-3) PUFA source is fish oil or algae oil.

The proportion of n-3 LC-PUFAs, more preferably DHA+EPA, of the total fatty acids is preferably 5 to 95 wt %, more preferably 10 to 80 wt %, most preferably 15 to 70 wt %. The present composition preferably comprises 5 to 95 wt % DHA based on total fatty acids, preferably 10 to 75 wt % DHA based on total fatty acids, more preferably 10 to 60 wt % DHA based on total fatty acids. The present composition preferably comprises 5 to 95 wt % EPA based on total fatty acids, preferably 10 to 75 wt % EPA, most preferably 15 to 60 wt %, based on total fatty acids. In one embodiment, the PUFAs, preferably DHA and/or EPA, most preferably DHA and EPA, are the sole fatty acid present and thus form 100 wt % of total fatty acids.

In terms of daily dosage, DHA is advantageously administered in a daily dose of 0.05-5 g/day, preferably 0.1-4 g/day, more preferably 0.5-2 g/day, most preferably 0.5-1.5 g/day. The amount of DHA in the composition or combination according to the invention is preferably such that the aforementioned daily doses are obtained. EPA is advantageously administered in a daily dose of 0.1-5 g/day, preferably 0.5-4 g/day, more preferably 1-3 g/day, most preferably 1.3-1.8 g/day. The amount of EPA in the composition or combination according to the invention is preferably such that the aforementioned daily doses are obtained.

The composition preferably provides for the administration of 500 to 5000 mg n-3 LC-PUFAs, more preferably DHA+EPA per day, more preferably 750 to 4000 mg per day, most preferably 1000 to 3000 mg per day. In case both DHA and EPA are present, the weight ratio of DHA to EPA is preferably between about 1:4 and about 10:1, preferably larger than 1, more preferably between about 2:1 and about 10:1, more preferably between about 3:1 and about 8:1.

In addition to the n-3 PUFAs, the composition may comprises n-6 PUFAs or n-6 LC-PUFAs (such as alpha-linolenic acid (ALA), linoleic acid (LA)). The ALA concentration is preferably maintained at levels less than 2.0 wt %, more preferably below 1.5 wt %, particularly below 1.0 wt %, based on the weight of all fatty acids. LA concentrations can be maintained at 20 to 30 wt %, based on the weight of all fatty acids, although in one embodiment the LA concentration is significantly reduced to an amount of below 15 wt % and even less than 10 wt %, based on total fatty acids. The LA concentrations are preferably at least 1 wt % of the fatty acids.

In one embodiment, the weight ratio n-3 PUFAs:n-6 PUFAs in the composition according to the invention is preferably in the range of 0.3 to 7, preferably in the range of 1.4:1 to 5.9:1, more preferably in the range of 3:1 to 5.5:1, most preferably in the range of 3:1 to 5:1, in particular less than 5:1. The amount of n-6 LC-PUFAs is preferably less than 50 wt %, preferably in the range of 5 to 40 wt %, more preferably 8 to 30 wt %, based on total weight of the fatty acids in the composition.

Further Components

The composition according to the invention may comprise further components, for example one or more selected from phospholipids, choline and B vitamin(s), preferably all three, and more preferably also antioxidants. The presence of (therapeutically effective amounts of) one or more of, preferably all of, choline, B vitamin(s), especially folic acid and vitamin B6, and antioxidants, especially vitamin C and/or E, is preferred, since brain damage has been suggested to lead to nutritional deficiencies in these components. As such, the presence of choline, B vitamin(s), especially vitamin B12, and antioxidants, especially vitamin C and/or E, may contribute to the general health of patients suffering from neuroinflammation. These components are typically present in therapeutically effective amounts. In one embodiment, no further active components are present and the composition or combination consists of (i) vitamin A, (ii) vitamin D and (iii) at least one omega-3 PUFA.

The present composition may comprise therapeutic amounts of phospholipids. Preferably, one or more phospholipid(s) is/are present in the composition according to the invention, preferably one or more phospholipid(s) selected from the group consisting of phosphatidic acid (PA), phosphatidylethanolamine (PE), phosphatidylcholine (PC), phosphatidylserine (PS) and phosphoinositide (PI). The present composition preferably comprises at least one phospholipid in an amount of 0.01 to 1 gram per 100 ml, more preferably between 0.05 and 0.5 gram per 100 ml, most preferably 80 to 600 mg per 100 ml. The at least one phospholipid is preferably provided by lecithin.

The present composition may comprise therapeutic amounts of choline. Choline may be present as such, or as choline equivalent in the form of e.g. salt or ester form, or any combination thereof. The choline salt is preferably selected from choline chloride, choline bitartrate, or choline stearate. The choline ester is preferably selected from a phosphatidylcholine and lyso-phosphatidyl choline. The present composition preferably provides for the administration of more than 50 mg choline per day, preferably 80 to 3000 mg choline per day, more preferably 100 to 2000 mg choline per day, most preferably 150 to 1000 mg choline per day. The present composition preferably comprises 80 mg to 3000 gram choline per 100 ml of the liquid composition, preferably 100 mg to 2000 mg choline per 100 ml, preferably 200 to 1000 mg choline per 100 ml composition, most preferably 200 mg to 600 mg choline per 100 ml. The above numbers are based on choline, the amounts of choline equivalents or sources can be calculated taking the molar equivalent to choline into account.

The present composition may comprise one or more B vitamin(s), preferably at least one, more preferably at least two, selected from the group of vitamin B6, vitamin B12 and vitamin B9. More preferably the composition comprises at least vitamin B6 and/or B9, most preferably vitamin B6, B9 and B12 Functional equivalents are encompassed within these terms. For instance, the term "vitamin B12" incorporates all cobalamin equivalents known in the art. The vitamin B is to be administered in a therapeutically effective dose.

Vitamin B6 is preferably present in an amount to provide a daily dosage in the range of 0.1 to 100 mg, in particular in the range of 0.5 to 25 mg, more in particular in the range of 0.5 to 5 mg. The present composition preferably comprises 0.1 to 100 mg vitamin B6 per 100 g (liquid) product, more preferably 0.5 to 5 mg vitamin B6 per 100 g (liquid) product, more preferably 0.5 to 5 mg vitamin B6 per 100 g (liquid) product. Vitamin B9 is preferably present in an amount to provide a daily dosage in the range of 50 to 5000 µg, in particular in the range of 100 to 1000 µg, more in particular in the range of 200 to 800 µg. The present composition preferably comprises 50 to 5000 µg vitamin B9 per 100 g (liquid) product, more preferably 100 to 1000 µg vitamin B9 per 100 g (liquid) product, more preferably 200 to 800 µg folic acid per 100 g (liquid) product. Vitamin B9 may be present as folate, which includes folic acid, folinic acid, methylated, methenylated and formylated forms of folates, their salts or esters (e.g. C1-6 alkyl ester), as well as their derivatives with one or more glutamic acid, and all in their reduced or oxidized form. Preferably, vitamin B9 is provided as folic acid. Vitamin B12 is preferably present in an amount to provide a daily dosage in the range of 0.5 to 100 µg, in particular in the range of 1 to 10 µg, more in particular in the range of 1.5 to 5 µg. The present composition preferably comprises 0.5 to 100 µg vitamin B12 per 100 g (liquid) product, more preferably 1 to 10 µg vitamin B12 per 100 g (liquid) product, more preferably 1.5 to 5 µg vitamin B12 per 100 g (liquid) product.

The present composition may further comprise antioxidants, preferably selected from vitamin C, vitamin E and selenium, preferably at least vitamin E. It is especially preferred that the composition comprises both vitamin C and vitamin E, most preferably the composition according to the invention comprises vitamin C, vitamin E and selenium. Antioxidants are preferably included in the composition according to the invention, as they may prevent oxidative damage resulting from dietary PUFAs.

Vitamin C includes functional equivalents thereof, and may be present in an amount to provide a daily dosage in the range of 20 to 2000 mg, in particular in the range of 30 to 500 mg, more in particular in the range of 75 to 150 mg. In one embodiment, vitamin C is present in an amount in the range of 20 to 2000 mg, in particular in the range of 30 to 500 mg, more in particular in the range of 75 to 150 mg per 100 ml of the composition.

Vitamin E refers to compounds having vitamin E activity as known in the art, typically tocopherol and/or an equivalent thereof. Vitamin E may be present in an amount to provide a daily dosage in the range of 10 to 300 mg, in particular in the range of 30 to 200 mg, more in particular in the range of 35 to 100 mg. Such amounts of vitamin E prevent oxidative damage to the injury site resulting from dietary PUFA present in the composition according to the invention. In one embodiment, tocopherol and/or equivalent is present in an amount in the range of 10 to 300 mg, in particular in the range of 30 to 200 mg, more in particular in the range of 35 to 100 mg per 100 ml of the composition. The term "tocopherol and/or an equivalent thereof", as used in this description, comprises tocopherols (e.g. alpha- and gamma-), tocotrienols, pharmaceutical and/or nutritional acceptable derivatives thereof and any combination thereof. The above numbers are based on alpha-tocopherol equivalents (alpha-TE), as recognized in the art.

The present composition preferably contains selenium. The antioxidant activity of selenium advantageously prevents and/or inhibits damages to the brain areas. Preferably the composition comprises 0.01 and 5 mg selenium per 100 ml liquid product, preferably 0.02 and 0.1 mg selenium per 100 ml liquid product. The amount of selenium administered per day is preferably more than 0.01 mg, more preferably 0.01 to 0.5 mg.

Application

The use, combination, composition or method according to the invention is for treating, reducing and/or preventing neuroinflammation and/or symptoms associated with neuroinflammation in a subject in need thereof. The invention also pertains to reducing microglia activation and/or to treating, reducing and/or preventing symptoms associated with excessive activation of microglia; and/or reducing the secretion of inflammatory cytokines, particularly IL-6, and/or to treating, reducing and/or preventing symptoms associated with excessive secretion of inflammatory cytokines. In the context of the invention, the prophylactic treatment includes reducing the risk or occurrence of neuroinflammation and/or its symptoms, microglia activation and/or symptoms thereof and cytokine secretion and/or symptoms thereof. In the context of the present invention, "neuroinflammation" may also be referred to as inflammation of the central nervous system (CNS). Herein, CNS refers to the brain and the spinal cord, preferably the present invention is directed to inflammation of the brain. In the context of the present invention, "secretion" (as in "secretion of inflammatory cytokines") and "release" (as in "release of inflammatory cytokines") are synonymous and used interchangeably.

Within the context of the invention, "symptoms associated with neuroinflammation" may be referred to as symptoms of neuroinflammation, and it is well within the skilled person's ambit to appreciate which are symptoms of neuroinflammation.

Throughout specification and claims, the term "treatment of neuroinflammation" includes prophylaxis and typically involves controlling neuroinflammation, preferably to the extent that (pathological or detriment) neuroinflammation is contained, confined or reduced. (Detriment or pathological) neuroinflammation may be acute or chronic neuroinflammation. In the context of the invention, treating and/or reducing neuroinflammation includes reducing the intensity of (detriment) neuroinflammation and/or reducing the duration of (detriment) neuroinflammation. In one embodiment, the reduction in duration of neuroinflammation corresponds to a reduction in duration compared to administration with individual components vitamin A, vitamin D or PUFAs, such as at least a 10% reduction, preferably at least a 25% reduction in duration. In one embodiment, the reduction in intensity of neuroinflammation corresponds to a reduction in secretion of inflammatory cytokines, preferably of IL-6, such as at least a 10% reduction, preferably at least a 20%, reduction in secretion compared to administration with vitamin A only, and/or at least a 10% reduction, preferably at least a 20%, reduction in secretion compared to administration with vitamin D only, and/or at least a 10% reduction, preferably at least a 20%, reduction in secretion compared to administration with PUFAs only. In one embodiment, the reduction in intensity of neuroinflammation corresponds to a reduction in release of NO, such as at least a 10% reduction, preferably at least a 30%, reduction in expression compared to administration with vitamin A only, and/or at least a 10% reduction, preferably at least a 30%, reduction in expression compared to administration with vitamin D only, and/or at least a 10% reduction, preferably at least a 30%, reduction in expression compared to administration with PUFAs only.

Increased levels of IL-6 and NO in the brain tissue or cerebrospinal fluid have been associated with neuroinflammatory disorders such as depression, schizophrenia, Alzheimer's disease (AD), Parkinson's disease, Multiple Sclerosis (MS), postoperative cognitive dysfunction (POCD), spinal cord injury (SCI), AIDS dementia complex (ADC), ischemia, stroke, traumatic brain injury (TBI), infection of the brain or central nervous system and brain tumours. Hence, in one embodiment, the neuroinflammation is associated with a disorders selected from depression, schizophrenia, Alzheimer's disease (AD), Parkinson's disease, Multiple Sclerosis (MS), postoperative cognitive dysfunction (POCD), spinal cord injury (SCI), AIDS dementia complex (ADC), ischemia, stroke, traumatic brain injury (TBI), infection of the brain or central nervous system and brain tumours. Likewise, in one embodiment, the subject is suffering from one or more disorders selected from depression, schizophrenia, Alzheimer's disease (AD), Parkinson's disease, Multiple Sclerosis (MS), postoperative cognitive dysfunction (POCD), spinal cord injury (SCI), AIDS dementia complex (ADC), ischemia, stroke, traumatic brain injury (TBI), infection of the brain or central nervous system and brain tumours. In one embodiment, the present use, method, combination or composition for use is for treating and/or preventing a disorder selected from depression, schizophrenia, Alzheimer's disease (AD), Parkinson's disease, Multiple Sclerosis (MS), postoperative cognitive dysfunction (POCD), spinal cord injury (SCI), AIDS dementia complex (ADC), ischemia, stroke, traumatic brain injury (TBI), infection of the brain or central nervous system and brain tumours. Preferred disorders in the context of the present invention are Alzheimer's disease (AD), postoperative cognitive dysfunction (POCD) and stroke.

In one embodiment, the neuroinflammation is chronic neuroinflammation or prolonged neuroinflammation, neuroinflammation regarded detrimental to the subject's health condition. The subject suffering from detrimental neuroinflammation or microglia activation is preferably suffering from a neurodegenerative disorder such as depression, schizophrenia, Alzheimer's disease (AD), Parkinson's disease and Multiple Sclerosis (MS), postoperative cognitive dysfunction (POCD), spinal cord injury (SCI), AIDS dementia complex (ADC), ischemia, stroke, traumatic brain injury (TBI), infection of the brain or central nervous system, brain tumours. In one embodiment, the composition according to the invention is for treating and/or preventing neuroinflammation, preferably for treating neuroinflammation, particularly reducing the duration and/or extent of neuroinflammation.

In one embodiment, the neuroinflammation is neuroinflammation of the central nervous system. Also, in the context of the invention, microglia activation and/or inflammatory cytokine secretion is typically reduced in the central nervous system. Excessive activation of microglia causes damage to brain tissue and to the blood-brain-barrier, causing neurodegenerative disorders.

The invention particularly concerns neuroinflammation caused by toxins or toxic metabolites, autoimmunity, aging, infection (e.g. bacterial or viral), traumatic brain injury, stroke, most preferably stroke-associated or stroke-induced neuroinflammation. In a preferred embodiment, the targeted subject suffers from stroke, has suffered from stroke, is at increased risk of stroke or is at increased risk of recurrent stroke. In one embodiment, the present use, method, combination or composition for use is for preventing and/or reducing the risk of recurrent stroke or a second or further occurrence of stroke. Likewise, in a preferred embodiment, the targeted subject has suffered from stroke.

In one embodiment, the use, combination, composition or method according to the invention is for therapeutically reducing the secretion of inflammatory cytokines and/or for treating, reducing and/or preventing symptoms associated therewith. The reduction or decrease in inflammatory cytokine secretion may take the form of a reduced amount (extent) of (excessive) expressed inflammatory cytokine and/or a reduced duration of (excessive) inflammatory cytokine secretion. Such reduction in inflammatory cytokine secretion typically occurs in the central nervous system. In a preferred embodiment of this use, the inflammatory cytokine is at least one of IL-4, IL-6, IL-10 and TNFα, preferably at least one of IL-6 and TNFα, most preferably at least IL-6. Inflammatory cytokines such as IL-6 are typically expressed by activated microglia during neuroinflammation, and lead to a prolonged state of increased oxidative stress. In one embodiment, the use, combination, composition or method according to the invention is for therapeutically reducing the release of NO and/or for treating, reducing and/or preventing symptoms associated therewith. The reduction or decrease in NO release may take the form of a reduced amount (extent) of (excessive) released NO and/or a reduced duration of (excessive) NO release. Such reduction in NO release typically occurs in the central nervous system. Excessive NO release has been shown to cause a neurotoxic effect. In the context of the present invention, "NO release" may also be referred to as "NO production".

The uses, combinations, compositions or methods as described above can be used as part of a nutritional therapy, nutritional support, as a medical food, as a food for special medical purposes or as a nutritional supplement. Administration of the composition according to the invention typically occurs during recovery and/or rehabilitation after the occurrence of neuroinflammation, and may be continued as long as negative effects thereof prolong. Although positive effects are already observed during the first week of administration, administration is preferably continued for at least 2 weeks, more preferably at least 4 weeks. Administration preferably starts at the first day after occurrence of neuroinflammation. The composition according to the invention can be consumed several times a day, preferably at one, two or three servings of 50-250 mL per day, typically of 125 mL or 200 mL per day during recovery and/or rehabilitation after the occurrence of a stroke. Preferred daily dosages are in the range of 100 to 500 mL, more preferably 125 to 375 mL, most preferably 125 to 300 mL.

Preferably, the composition is enterally administered. Administration occurs preferably at least one time per day, although alternative dosage regimes can be determined from these numbers.

LIST OF FIGURES

Figure 1B:
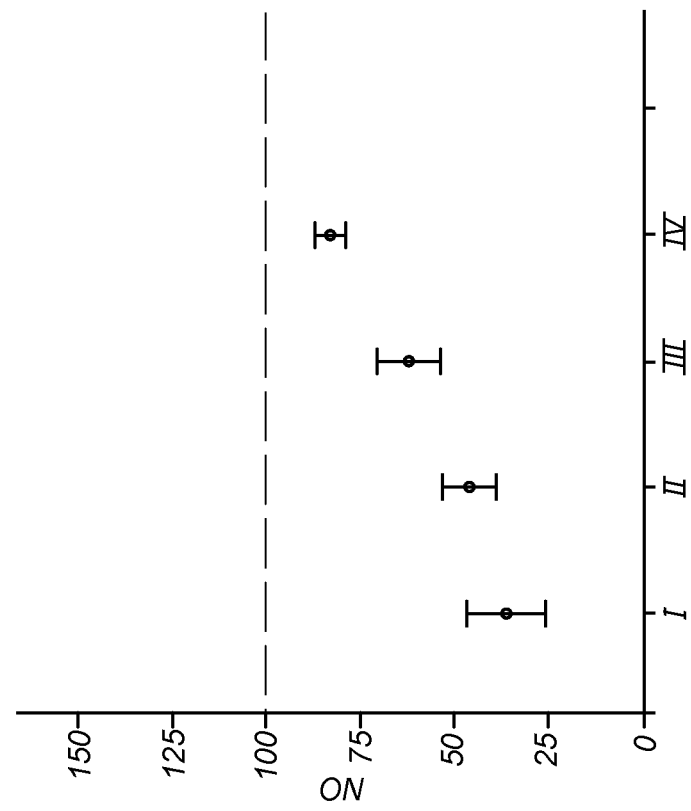

FIG. 1 depicts the effect of individual nutrients on LPS-induced NO and IL-6 release as demonstrated in Example 1. NO (FIG. 1A) and IL-6 (FIG. 1B) release from LPS-activated microglia upon incubation with different nutrients (I=vitamin A; II=vitamin D; III=DHA; IV=EPA) is given as percentage of NO release from LPS-activated microglia not incubated with a nutrient (control), which is set at 100%. Compared to the control, nutrients I-III exhibited significantly reduced NO and IL-6 release ($p<0.001$).

Figure 2A:
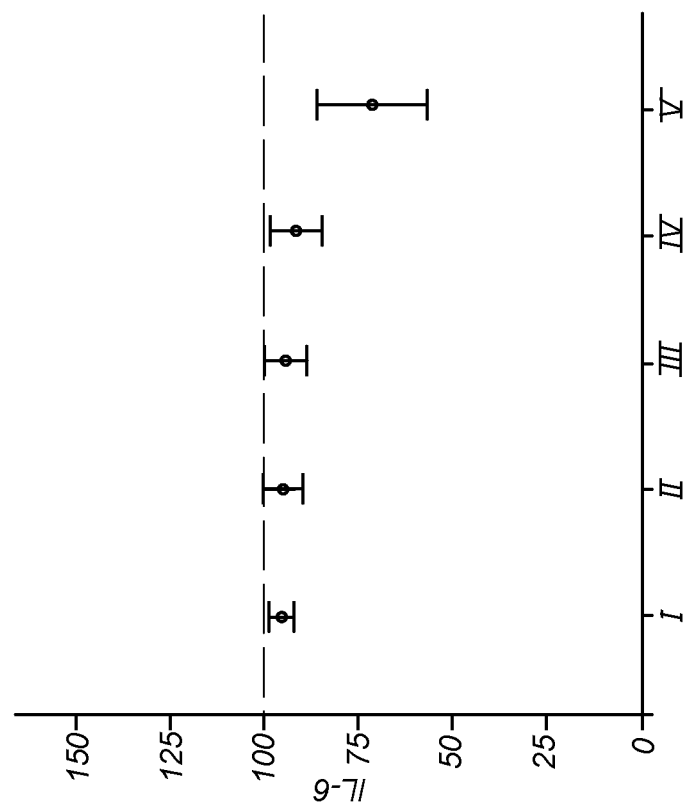
Figure 2B:
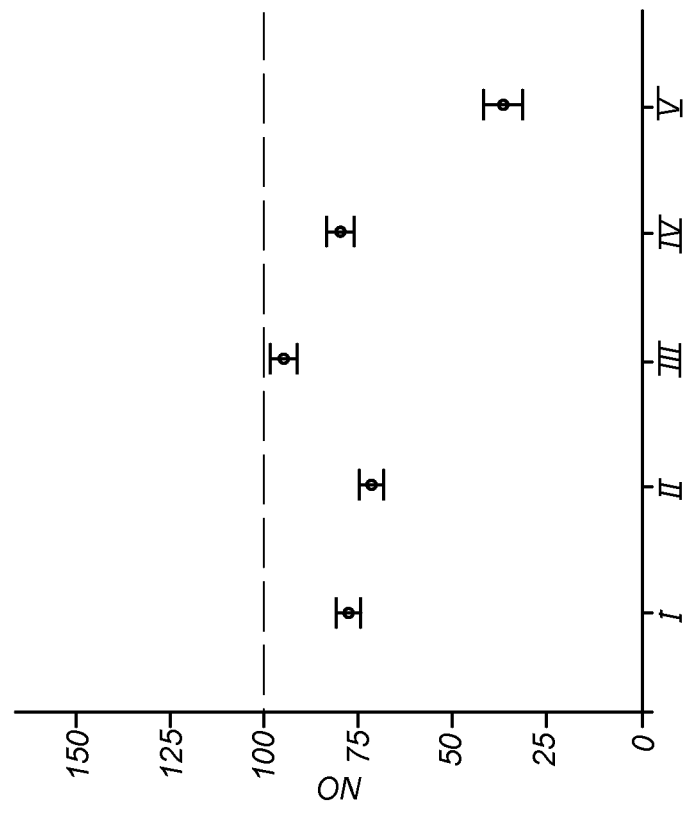

FIG. 2 depicts the effect of individual nutrients and of the combination of nutrients on LPS-induced NO and IL-6 release as demonstrated in Example 2. NO (FIG. 2A) and IL-6 (FIG. 2B) release from LPS-activated microglia upon incubation with different nutrients (I=vitamin A; II=vitamin D; III=DHA; IV=EPA; V=vitamin A+vitamin D+DHA+EPA) is given as percentage of NO release from LPS-activated microglia not incubated with a nutrient (control), which is set at 100%. Combination of nutrients V exhibited significantly reduced NO release compared to the individual ingredients I-IV ($p<0.001$).

EXAMPLES

Materials En Methods for Examples 1 and 2

Reagents: The following substances were purchased from Sigma Aldrich and used without further purification: lipopolysaccharide (LPS, from *Escherichia coli* 055:B5), vitamin B6, B9 (folic acid), vitamin B12, vitamin A, vitamin D3 in a form of 7-dehydrocholesterol/25-OH vitamin D3 (100 μg/ml in ethanol), cis-4,7,10,13,16,19-docosahexaenoic acid (DHA), cis-5,8,11,14,17-eicosapentaenoic acid (EPA).

BV-2 cell cultures: BV-2 cells were obtained from IRCCS (Azienda Ospedaliera Universitaria San Martino—IST Istituto Nazionale per la Ricerca sul Cancro, Genova, Italy). BV-2 cell lines are immortalized cell lines derived from C57bl/6 mouse. These are considered to closely resemble the physiology of primary microglia cells and form a well-established model for investigation in vitro (Henn et al., ALTEX, 2009, 26, 83-94). Lipopolysaccharide (LPS), an endotoxin derived from the cell wall of gram negative bacteria, is the most widely used agent to activate immune cells. Cells were cultured in Dulbecco's Modified Eagle Medium (DMEM, Gibco) supplemented with 10% of heat-inactivated fetal bovine serum (Invitrogen), 10,000 units/ml penicillin (Gibco), 10,000 μg/ml streptomycin (Gibco) and 200 mM L-glutamine (Gibco) and maintained at 37° C. and 5% $CO_2$. Twenty-four hours before the experiment, cells were plated on 96 well plates (Corning) at a cell density of approximately 20,000 cells/well and maintained in DMEM supplemented with 2% fetal bovine serum, 10,000 units/ml penicillin, 10,000 μg/ml streptomycin and 200 mM L-glutamine, for the duration of the experiment.

Cell viability: Cell proliferation and viability were assessed with 2,3-bis(2-methoxy-4-nitro-5-sulfophenyl)-2H-tetrazolium-5-carboxanilide inner salt (XTT, Sigma) at a concentration of 1 mg/ml. Phenazine methosulfate (PMS, Sigma) at a concentration of 200 mg/ml was added as an electron coupling reagent. The XTT/PMS solution in sterile water (100 μl) was added to each well. After 2 h, the absorbance was measured at 450 nm (and 690 nm as a reference). The absorbance was corrected for the number of cells. The viability test was repeated for each experiment as a within plate control. The results of experiments, in which the cell viability was below 85% of that of the untreated control cells, were excluded from the data analysis.

Griess assay (nitric oxide release): Cells were treated for 24 h with different combinations of nutrients. This treatment was followed by exchanging the medium for fresh medium with LPS (50 ng/ml) combined with the same nutrients. After incubation for 24 h, media were collected for measurement of NO release. The stable product of NO released by the BV-2 cells is $NO_2^-$. The concentration of $NO_2^-$ was measured with a Griess assay Kit (Promega) according to the manufacturer's instructions. Data were corrected for cell viability (the viability of untreated control cells represented 100% of viability). Data are represented as percentage of the NO released by cells stimulated only with LPS. To assess variability between the tests, data from the treatment with LPS alone were pooled and an average release between experiments was calculated for NO. For treatment with LPS alone, the NO release is represented as the percentage of the average release between experiments.

ELISA (IL-6): Cells were treated for 24 h with different combinations of nutrients. Subsequently, the medium was removed and cells were incubated for 24 h in fresh medium with LPS (50 ng/ml) combined with the same nutrients. Media were collected for measurement of IL-6 release. Collected samples were stored at −80° C. until further analysis. The cytokine levels were assessed using ELISA MAX™ Deluxe from Biolegend according to the manufacturer's protocol. Data were corrected for cell viability. Data are represented as percentage of the IL-6 released by cells stimulated only with LPS. To assess variability between the tests, data from the treatment with LPS alone were pooled and an average release between experiments was calculated for IL-6. For LPS alone treatment the IL-6 release is represented as the percentage of the average release between experiments.

Statistical analysis: All experiments were performed at least in triplicate. The data are presented as dots representing means and bars representing standard error mean (SEM). Due to the small sample size, non-parametric statistical tests were used. Data were analyzed with the Kruskal-Wallis H test and if the statistical significance was reached, Mann Whithey U test with Bonferroni-Holm post-hoc correction to allow multiple comparisons was performed. A difference was considered statistically significant when the probability (p) was <0.05.

Example 1: Effect of Individual Nutrients

BV-2 cells were pretreated for 24 h with different nutrients: (I) vitamin A (1.75 μM); (II) vitamin D (1 μg/ml); (III) DHA (20 μM); (IV) EPA (20 μM); (V) vitamin B6 (29 μM, including 19 μM already present in the culture medium); (VI) folic acid (24 μM, including 9 μM already present in the culture medium); (VII) vitamin B12 (0.2 μM). This was followed by 24 h incubation with LPS (50 ng/ml) combined with the same nutrients. Media were collected for measurement of NO release with the Griess assay (FIG. 1A) and IL-6 release with ELISA (FIG. 1B). NO and IL-6 levels are presented as the percentage of the concentration produced by cells treated with LPS alone (LPS control, dashed line).

All graphs represent the results from 4 independent experiments (mean±SEM). Data were statistically analyzed with Kruskal-Wallis H test, followed by a Bonferroni-Holm post-hoc test. A difference was considered statistically significant when p<0.05.

The nutrients were used in high non-toxic concentrations, obtained from dose-effect curves of single substances and their mixture, when a concentration in which cell viability did not decrease below 90% as compared to untreated controls. In a similar way, a dose-effect curve for LPS was obtained from NO release measurements in order to select a half maximal effective concentration (EC50). The release of the proinflammatory mediator nitric oxide (NO) by activated BV-2 cells was measured with the Griess assay. Cells only exposed to the culture medium or to the medium supplemented with nutrients did not show any detectable release of NO (data not shown). A 24 h treatment of BV-2 cells with LPS (50 ng/ml) caused a robust release of NO. In order to investigate the potency of nutrients to inhibit the LPS-induced NO release, BV-2 cells were pre-treated for 24 h with nutrients and subsequently co-treated with LPS and the same nutrients for another 24 h. Vitamins B6, B9 and B12 as well as the amino acids L-tryptophan and L-cysteine did not cause any significant effect on LPS-induced NO release in these experiments (data not shown). The fatty acid DHA caused a significant decrease in the NO release, 68% (IQR, 49-77%, p=0.036), as compared to LPS treated-controls (FIG. 1A). The fatty acid EPA caused a decrease in NO release to 80% (IQR, 75-91%, p=0.115), which was not statistically significant, while mixing DHA and EPA caused decrease in NO release to 61% (IQR 43-66%, data not shown). The most potent anti-inflammatory nutrients in this assay were vitamins A and D (FIG. 1A). Vitamin D significantly decreases NO release to 43% (IQR 36-55%; p=0.032) relative to LPS-treated control cells. A significant anti-inflammatory effect was also observed by the treatment with vitamin A. Vitamin A significantly decreased NO release to 39% of LPS-treated controls (IQR 20-52.4%; p=0.024). Therefore it was concluded that from all nutrients tested, vitamins A and D and DHA are the most potent to decrease LPS-induced NO release.

The anti-inflammatory effect of the nutrients on LPS-induced IL-6 production by BV-2 cells was investigated with ELISA. LPS treatment caused a high increase in IL-6 release from BV-2 cells in a concentration-dependent manner. The optimal LPS concentration (inducing approximately 50% of the maximal release) for our experiments was selected based on the concentration-dependent curve of IL-6 release (data not shown). Similarly to the effects observed on NO release, vitamins B6, B9 and B12, as well as the amino acids L-tryptophan and L-cysteine did not cause any significant effects on LPS-induced IL-6 release in these experiments (data not shown). The inhibition of IL-6 release was more responsive (FIG. 1B). DHA significantly decreased the release of IL-6 by LPS-stimulated BV-2 cells to 68% (IQR 49-77%, p=0.032, n=4). The fatty acid EPA caused a decrease in IL-6 release to 70% (IQR, 67-96%, p=0.7, n=4) (FIG. 1B), but this was not statistically significant. While mixing DHA and EPA caused a decrease in IL-6 release to 51% (IQR 38-54%, data not shown). Vitamins A and D decreased IL-6 release to 42% (IQR 39-58%, p=0.024, n=4) and 43% (IQR 21-57%, p=0.024, n=4), respectively (FIG. 1B).

Taken together, these data show that vitamins A and D—and to a lesser extent DHA and EPA—exhibited an anti-inflammatory effect on LPS-stimulated BV-2 cells.

Vitamins B and amino acids L-cysteine and L-tryptophan did not have an anti-inflammatory effect on LPS-activated BV-2 cells.

Example 2: Effect of Combined Nutrients

BV-2 cells were pretreated for 24 h with different combinations of nutrients: (I) vitamin A (0.583 µM); (II) vitamin D (0.1 µg/ml); (III) DHA (6.67 µM); (IV) EPA (20 µM); (V) vitamin A (0.583 µM)+vitamin D (0.1 µg/ml)+DHA (6.67 µM)+EPA (20 µM). This was followed by 24 h incubation with LPS (50 ng/ml) combined with the same nutrients. Media were collected for measurement of NO release with the Griess assay and IL-6 release with ELISA. NO (FIG. 2A) and IL-6 (FIG. 2B) levels are presented as the percentage of the concentration produced by cells treated with LPS alone (LPS control). The level of NO and IL-6 for LPS control (100%) is indicated on each graph with the dashed line. All graphs represent the results from five independent experiments (mean±SEM). Data were statistically analysed with Kruskal-Wallis H test. A difference was considered statistically significant when p<0.05. To test for differences between the single nutrients and the mixture containing vitamin A, D and fatty acids DHA and EPA, a post hoc test with Bonferroni-Holm correction was performed. A difference was considered statistically significant when p<0.05.

As shown in FIG. 2A, single nutrients used in lower concentrations hardly caused any effect on NO release, while the combination of these substances in the same concentrations caused a reduction in the NO release to 37% (IQR 28.0-45.7%) of the release by untreated LPS-stimulated control cells. The decrease in NO release observed for the combination of nutrients was significantly different from the effects observed for each nutrient used separately (after the Bonferroni-Holm correction p=0.032). In a similar way, single nutrients in lower concentrations caused no significant decrease in IL-6 release. Combining the substances resulted in decrease of IL-6 to 84% (IQR, 54.1-88.9) as compared to LPS-stimulated controls.

The invention claimed is:
1. A method for treating, reducing and/or preventing neuroinflammation in a subject in need thereof, comprising administering to the subject a composition or combination comprising therapeutically effective amounts of (i) vitamin A, (ii) vitamin D, and (iii) DHA and EPA, wherein the vitamin A is administered in a daily dose of 0.05-3 mg/day, wherein the vitamin D is administered in a daily dose of 0.1-100 µg/day, and wherein the DHA is administered in a daily dose of 500 to 5000 mg/day.

2. The method according to claim 1, wherein the neuroinflammation is associated with a disorder selected from depression, schizophrenia, Alzheimer's disease (AD), Parkinson's disease, Multiple Sclerosis (MS), postoperative cognitive dysfunction (POCD), spinal cord injury (SCI), AIDS dementia complex (ADC), ischemia, stroke, traumatic brain injury (TBI), infection of the brain or central nervous system and brain tumours and/or said subject suffering from one or more disorders selected from depression, schizophrenia, Alzheimer's disease (AD), Parkinson's disease, Multiple Sclerosis (MS), postoperative cognitive dysfunction (POCD), spinal cord injury (SCI), AIDS dementia complex (ADC), ischemia, stroke, traumatic brain injury (TBI), infection of the brain or central nervous system and brain tumours.

3. The method according to claim 2, wherein the disorder is selected from Alzheimer's disease (AD), postoperative cognitive dysfunction (POCD) and stroke.

4. The method according to claim 3, wherein the neuroinflammation is stroke-associated neuroinflammation and/or in a subject suffering from stroke or being at increased risk of stroke.

5. The method according to claim 1, wherein the neuroinflammation is chronic neuroinflammation.

6. The method according to claim 1, wherein the treating, reducing and/or treating and/or preventing comprises reduction of the intensity of neuroinflammation and/or reduction of the duration of neuroinflammation.

7. The method according to claim 1, wherein the treating, reducing and/or preventing comprises reduction of microglia activation and/or reduction of the secretion of inflammatory cytokines.

8. The method according to claim 7, wherein the cytokines are TNF-α and/or IL-6.

9. The method according to claim 1, wherein the vitamin A is administered in a daily dose of 0.5-1.5 mg/day.

10. The method according to claim 1, wherein the vitamin D is administered in a daily dose of 5-15 µg/day.

11. The method according to claim 1, wherein the DHA is administered in a daily dose of 0.5-1.5 g/day.

12. The method according to claim 1, wherein the composition further comprises choline.

13. The method according to claim 12, wherein the composition further comprises B vitamin(s).

14. The method according to claim 1, wherein the composition further comprises phospholipids, choline, B vitamin(s) and antioxidants.

* * * * *